United States Patent

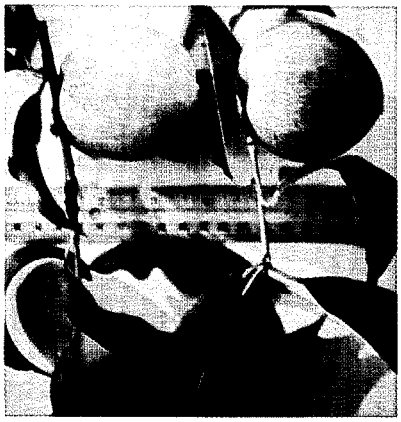
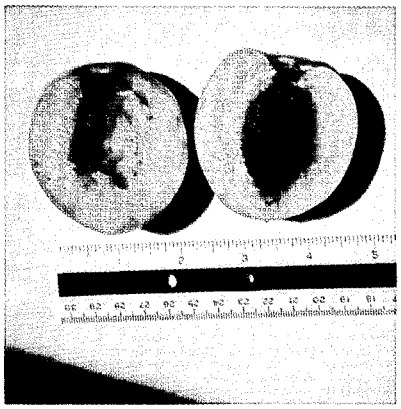

Plant Pat. 3,964

Patented Oct. 26, 1976

3,964

NECTARINE TREE

Henry G. Wong, 900 Jackson St., Oakland, Calif. 94607

Filed Nov. 4, 1975, Ser. No. 628,644

Int. Cl.[2] A01H 5/03

U.S. Cl. Plt.—41 1 Claim

ABSTRACT OF THE DISCLOSURE

A nectarine tree, of medium to large size, which needs little sunlight, and which is a productive bearer of medium size, nearly globose, late ripening clingstone fruit having flesh yellow throughout, with yellow skin partly overspread with red.

BACKGROUND OF THE VARIETY

For several years I have engaged in a breeding and propagation program in three home orchards under my ownership and control in Oakland, Alameda County, Calif. One purpose of such program has been to provide improved varieties of fruit trees, and the present variety is one result of my endeavors.

ORIGIN OF THE VARIETY

The present variety of nectarine tree was discovered by me as a seedling in my home orchard at my residence. It was first noted in my records in 1972 and designated therein as Peach S–1. It is of unknown genetic parentage. There were no trees on the property in April 1970, so the seedling probably sprouted in 1971 or 1972. This seedling bore its initial crop (around 22 fruits) in 1975. The fruits were of superior flavor compared to most other nectarines then on the market. The flavor was also significantly fuller than that of plum and peach fruits from adjacent trees of Friar plum (unpatented) and Babcock peach (unpatented), all three trees being within ten feet of the northeast side of a four story building.

ASEXUAL REPRODUCTION OF THE VARIETY

On or about January 28, 1973 I grafted a scion of this instant variety onto a mature peach tree in one of my other home orchards in Oakland, Calif., and such reproduction has run true to the orginal tree. Both the original tree and the graft reproduction produced first crops in 1975.

SUMMARY OF THE VARIETY

The present variety of nectarine tree, which is of medium to large size, spreading, upright form, is a productive bearer of medium, relatively uniform, clingstone fruit of yellow flesh, and yellow skin partially overspread with red. Compared to other late season clingstones, this variety is particularly characterized by the flesh being yellow throughout (including the pit), and by the ability of the tree to produce fruit of pleasing flavor and aroma with less than full sunlight.

BRIEF DESCRIPTION OF THE DRAWING

The drawing is an illustration, by photographic reproduction in color, of twigs with leaves and fruit remaining attached; other fruits being detached and cut in half, with the stone removed from one half and remaining in the other.

DESCRIPTION OF THE VARIETY

The botanical details of this new and distinct variety of nectarine tree are as follows: Color identifications are referenced to *ISCC–NBS Color Name Charts Illustrated with Centroid Colors* issued as a supplement to *National Bureau of Standards Circular 553, ISCC–NBS Method of*

*Designating Color and a Dictionary of Color Names,* except where reference is to *RHS Colour Chart* published in 1966 by the Royal Horticultural Society of London (hereafter abbreviated as RHS) or where common color terms are used.

Tree:
- Size—Medium
- Vigor—Vigorous
- Form—Spreading, upright
- Density—Open to medium
- Production—Productive
- Bearing—Unknown
- Hardiness—Unknown
- Fruit drop—Almost none Trunk:
- Size—Medium
- Texture—Medium
- Color—Brown Branches:
- Size—Medium
- Texture—Medium
- Color—Green and red when young; brown when older
- Lenticels—Medium in number and size Leaves:
- Size—Average length 4"; average width 1⅜".
- Color—Top side, RHS 146A yellow-green (closer to NBS 125 moderate olive green than NBS 127 grayish olive green); bottom side—RHS 146B lighter yellow green (approx. NBS 120 moderate yellow green); heavy midrib on lower surface, RHS 145C light yellow green, (NBS closer to 119 light yellow green than 121 pale yellow green).
- Form—Lanceolate
- Thickness—Equal to or thicker than average peach
- Texture—Smooth
- Margin—More serrate than crenate
- Glands—Reinform and alternate; total varies from one to five (average 3) positioned usually two (varies from none to three) on petiole next to blade and in many instances 1 or 2 on the blade margin near petiole
- Petiole—Medium thickness, average length ½ inch
- Stipules—None.

Flower buds:
- Size—Length ¾ inches, diameter ½ inch, stem length ⅛ inch
- Form—Obtuse and plumb Flowers:
- Blooming period—First bloom Mar. 10, 1975. Full bloom Mar. 19, 1975, about 10 days after Babcock peach (unpatented)
- Positioning—Singly rather than in clusters, but two or three flowers may be within one inch of branch length
- Size—Spread across petal 1⅝–2 inches
- Color—Pale pink (NBS 7)
- Petals—Mostly 5 in number, some 6, obtuse shape
- Pedicel—½ inch length
- Stamens—Color strong reddish purple (NBS 237) 26–31 in number, length ½–⅝ inch
- Styles—¼ inch longer than stamens; color yellow
- Sepals—Mostly 5, some 6, moderate yellowish green (NBS 136) with overlay on back side of dark grayish red (NBS 20)

Fruit:
- Maturity when described—Eating ripe, Aug. 31, 1975 after a mild winter, about one month after adjacent Babcock peach (unpatented) and about three weeks after adjacent Friar plum (unpatented)

Date of first picking—Aug. 26, 1975
Date of last picking—Sept. 9, 1975
Size—Uniform, medium, average diameter axially 2¼", average transversely in suture plane 1⅞"
Form—Uniform, nearly globose, almost symmetrical
Suture—Shallow, extends from base to beyond apex
Cavity—Rounded to slightly enlongated in suture plane
Base—Slightly oval
Apex—Short Skin:
Thickness—Medium
Texture—Smooth
Tendency to crack—almost none
Down—None
Color—Ground color is RHS 15D (less vivd than NBS 67 brilliant yellow orange) overspread one fourth to three fourths with deep reddish orange (RHS 34A), shading to deep red (NBS 13) (RHS 46A)

Flesh:
Fibers—None
Texture—Firm, meaty
Juice—Juicy
Ripens—Evenly
Flavor—Pleasing, mildly subacid, delicate
Aroma—Pleasing
Eating quality—Good to best
Color—Yellow orange (RHS 16C) throughout, less vivid than NBS 67 brilliant yellow orange. No red next to stone Stone:
Type—Cling
Size—Medium, length 1⅛" to 1⅜", breath ¾" to ⅞", thickness ⅝" to 11/16"
Form—Obovate, tip acuminate
Base—Oblique
Apex—Acuminate
Sides—Almost equal, one slightly more curved than the other
Surface—Furrowed near apex toward ventral edge; pitted from base toward center and dorsal edge
Dorsal edge—Thin, with groove running from base along half of edge
Ventral edge—Thick, with deep furrows and wing toward base and with multiple ridges toward apex
Tendency to split—None Color—Greyed orange (RHS 168D) mostly covered by deep red purple (RHS 61B)
Use: Market—Dessert
Resistance to insects and diseases: No unusual susceptibilities noted The nectarine tree and its fruit herein described may vary in slight detail due to differences in climate, soil, pruning, fertilization or other growing conditions. The present description is of the variety as grown within ten feet of the northeast side of a four story building in Oakland, Calif.

For example, with particular reference to growth habit of the tree, the aforementioned Babcock peach tree adjacent to the instant variety tree was of medium size, medium vigor and more upright than spreading. In comparison, Babcock peach when grown in full sunlight is usually of "medium to large size, vigorous and inclined to be spreading rather than upright in habit of growth," as introduced in University of California Agriculture Experiment Station circular 328 (January 1933). Also at that same location with minimal sunlight, the aforementioned adjacent Friar plum tree was of small size and low to medium vigor. In comparison, Friar plum when grown in full sunlight is generally very vigorous, as reported in the release notice on Friar plum issued Mar. 19, 1968 by USDA Agricultural Research Service, Crops Research Division. Based on these comparisons, the instant variety may therefore be expected to develop, when grown under full sunlight, a tree habit of larger size, more vigor, and more spreading and less upright form than when grown under minimal sunlight.

I claim:

1. A new and distinct variety of nectarine tree, substantially as illustrated and described, identified by the characteristics enumerated above, and characterized particularly as to novelty in comparison to other clingstone nectarines by the season of ripening, by the bearing of fruit having yellow skin partly overspread with red, flesh of pleasant flavor and aroma, with yellow color throughout including the pit, a stone with characteristics as hereinabove described, and by the ability of the tree to produce such fruit with limited sunlight.

No references cited.

ROBERT E. BAGWILL, Primary Examiner